United States Patent [19]

Woo et al.

[11] Patent Number: 4,943,640

[45] Date of Patent: Jul. 24, 1990

[54] PREPARATION OF 5-(1-ALKYL-CARBONYLOXY)ALKYLPYR-ROLIDIN-2-ONE

[75] Inventors: Edmund P. Woo; Michael J. Mullins, both of Midland, Mich.

[73] Assignee: The Dow Chemical Company, Midland, Mich.

[21] Appl. No.: 169,691

[22] Filed: Mar. 18, 1988

Related U.S. Application Data

[63] Continuation-in-part of Ser. No. 542,293, Oct. 14, 1983, abandoned.

[51] Int. Cl.$^5$ .......................................... C07D 207/277
[52] U.S. Cl. .................................. 548/551; 548/530; 548/531; 548/533; 548/544
[58] Field of Search ......................................... 548/551

[56] References Cited

FOREIGN PATENT DOCUMENTS 2028307 3/1980 United Kingdom .

OTHER PUBLICATIONS

*Chem. Abstracts*, vol. 82, 97983b, p. 438 (1975).
Lepschy et al., *Justus Liebigs Ann. Chem.*, 1753 (1974).

*Primary Examiner*—David B. Springer

[57] ABSTRACT

The invention is a process for the preparation of a 5-(1-alkylcarbonyloxy)alkylpyrrolidin-2-one which comprises contacting a N-alkylcarbonyl-5-alkylcarbonyl-pyrrolidin-2-one with hydrogen in the presence of a catalytic amount of a hydrogenation catalyst under conditions such that a 5-(1-alkylcarbonyloxy)alkylpyrrolidin-2-one is prepared.

19 Claims, No Drawings

PREPARATION OF 5-(1-ALKYL-CARBONYLOXY)ALKYLPYRROLIDIN-2-ONE

CROSS-REFERENCE TO RELATED APPLICATION

This application is a continuation-in-part of application Ser. No. 542,293, filed Oct. 14, 1983, abandoned.

BACKGROUND OF THE INVENTION

This invention relates to the preparation of 5-(1-alkylcarbonyloxy)alkylpyrrolidin-2-ones.

The 5-(1-alkylcarbonyloxy)alkylpyrrolidin-2-ones are useful as intermediates in the preparation of pharmacologically active compounds. More particularly, these compounds can be converted to 5-(1,2-ethylenically unsaturated)alkylpyrrolidin-2-ones, which can then be converted to a 4-amino-5-alkenoic acid (see Gittos et al., U.S. Pat. No. 4,235,778, incorporated herein by reference). 4-Amino-5-alkenoic acids are pharmacologically active compounds. One 4-amino-5-alkenoic acid is 4-amino-5-hexenoic acid which is an irreversible inhibitor of y-aminobutyric acid transaminase, rendering it useful in the treatment of disorders of the central nervous system function (see Metcalf et al., U.S. Pat. No. 3,960,927, incorporated herein by reference).

Presently known processes for the preparation of 5-(1,2-ethylenically unsaturated)alkylpyrrolidin-2-ones require costly reagents and complicated processing schemes. What is needed is a relatively simple process for the preparation of a precursor to the 5-(1,2-ethylenically unsaturated)alkylpyrrolidin-2-one in which relatively available and inexpensive starting reagents are used, and wherein the precursor can be pyrolyzed to the desired 5-(1,2-ethylenically unsaturated)alkylpyrrolidin-2-one.

SUMMARY OF THE INVENTION

The invention is a process for the preparation of a 5-(1-alkylcarbonyloxy)alkylpyrrolidin-2-one which comprises contacting a N-alkylcarbonyl-5-alkylcarbonylpyrrolidin-2-one with hydrogen in the presence of a catalytic amount of a hydrogenation catalyst under conditions such that a 5-(1-alkylcarbonyloxy)alkylpyrrolidin-2-one is prepared.

Surprisingly, a process for the preparation of a compound which can be pyrolyzed to a 5-(1,2-ethylenically unsaturated)alkylpyrrolidin-2-one in which the starting reagents are relatively available and inexpensive has been discovered. In addition to their utility as precursors to pharmacologically active compounds, the products of the process of this invention are also useful as solvents for organic compounds which are soluble in N-methylpyrrolidinone and as monomers for copolymerization with other vinyl monomers.

DETAILED DESCRIPTION OF THE INVENTION

Preferred N-alkylcarbonyl-5-alkylcarbonylpyrrolidin-2-ones include those which correspond to the formula

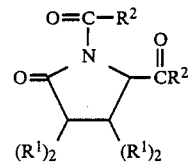

and the 5-(1-alkylcarbonyloxy)alkylpyrrolidin-2-ones include those which correspond to the formula

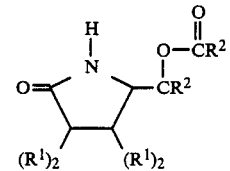

wherein $R^1$ is separately in each occurrence hydrogen, $C_{1-20}$ alkyl or $C_{1-20}$ alkyl substituted with one of the following: aryl, cycloalkyl, a thioalkyl, tert-amino, alkoxy, aryloxy, aralkoxy, carbonyldioxyalkyl, carbonyldioxyaryl, carbonyldioxyaralkyl, alkoxycarbonyl, aryloxycarbonyl, aralkoxycarbonyl, alkylcarbonyl, arylcarbonyl, aralkylcarbonyl, alkylsulfinyl, arylsulfinyl, aralkylsulfinyl, alkylsulfonyl, arylsulfonyl or aralkylsulfonyl group; and $R^2$ is $C_{1-20}$ alkyl.

$C_{1-20}$ alkyl includes straight- and branched-chain alkyls such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl refers to methyl, ethyl, propyl, butyl and pentyl groups.

Alkylcarbonyl refers herein to an organic radical wherein a alkyl group is bonded to a carbonyl moiety, and is represented by the formula

wherein R is alkyl. Alkylcarbonyloxy refers herein to an organic radical wherein a alkyl group is bonded to a carbonyl moiety which is further bonded to an oxygen atom, and is represented by the formula

wherein R is alkyl.

In this invention $R^1$ is preferably hydrogen or $C_{1-20}$ alkyl, more preferably hydrogen or $C_{1-5}$ alkyl and most preferably hydrogen. $R^2$ is preferably $C_{1-20}$ alkyl, more preferably $C_{1-5}$ alkyl and most preferably methyl. In one preferred embodiment wherein $R^1$ is hydrogen and $R^2$ is methyl, the product is 5-(1-acetyloxyethyl)pyrrolidin-2-one.

In general a 5-(1-alkylcarbonyloxy)alkylpyrrolidin-2-one is prepared by a process which comprises contacting a N-alkylcarbonyl-5-alkylcarbonyl-2-pyrrolidin-2-one with hydrogen in the presence of a hydrogenation catalyst.

Any catalyst which is known to those skilled in the art as a hydrogenation catalyst is useful as the catalyst in this invention. Preferred catalysts include Group VIII metals, rhenium, chromium or iron, or compounds thereof which are catalytic. More preferred catalysts are palladium or platinum, with platinum being most preferred.

The catalyst may be used in either a homogeneous or heterogeneous form. Heterogeneous catalysts are preferred.

In the heterogeneous form it is preferable that the catalyst be supported. Any support which has structural integrity and can form an affinity for the catalyst may be used. Among preferred supports are clays, aluminas, zeolites, silicas, silica gels, silicalite, activated carbons and diatomaceous earth. More preferred supports are zeolites, silicas, aluminas or activated carbon, with aluminas being most preferred. The catalyst can be loaded on the support in an amount which is catalytic under reaction conditions. Preferably the catalyst is loaded on the support in an amount of between about 0.1 and 25 percent by weight, preferably between about 0.5 and 10 percent by weight and most preferably between about 1 and 5 percent by weight.

In a homogeneous process, the catalyst can be present in any concentration which catalyzes the reaction claimed herein. Generally, a concentration of 0.1 to 10 mole percent based on the N-alkylcarbonyloxy-5-alkylcarbonyloxypyrrolidin-2-one is preferred, more preferably between about 0.5 and 2 mole percent.

This process may be run in either the vapor or the liquid phase. The liquid phase is preferred.

Any temperature at which the reaction proceeds is suitable for this invention. Preferably, the temperature is between about 25° C. and 200° C., more preferably between about 50° C. and 150° C. and most preferably between about 80° C. and 100° C.

Any pressure at which the reaction proceeds is suitable for this invention. Preferably, pressures are between about 14.7 and 3,000 psi, more preferably between 50 and 1,500 psi and most preferably between about 800 and 1,000 psi. Generally, the reactor is pressurized with hydrogen, although an inert gas such as nitrogen could be used to pressurize the reaction vessel.

A sufficient amount of hydrogen to convert the N-alkylcarbonyl-5-alkylcarbonylpyrrolidin-2-one to a 5-(1-alkylcarbonyloxy)alkylpyrrolidin-2-one is used. At least 1 mole of hydrogen per mole of starting compound is needed. In most cases, a large molar excess of hydrogen is used as hydrogen is also used to pressurize the reaction vessel. In the embodiment wherein $R^1$ in the N-alkylcarbonyl-5-alkylcarbonylpyrrolidin-2-one contains nonaromatic double or triple bonds, the double or triple bonds will undergo hydrogenation to prepare a product wherein $R^1$ or $R^2$ do not contain nonaromatic double or triple bonds.

It is preferable to run this reaction in an organic solvent. Suitable organic solvents are those in which the N-alkylcarbonyloxy-5-alkylcarbonyloxypyrrolidin-2-one is soluble, which is inert to the reactants and is not reducible by hydrogen under the reaction conditions. Among the preferred solvents are alcohols, ethers, esters, aromatic hydrocarbons or carboxylic acids. More preferred solvents are carboxylic acids, with monocarboxylic acids such as acetic acid most preferred. Sufficient solvent to dissolve the reactants is used. Preferable amounts of solvent are between about 1 and 100 milliliters per gram of substrate, more preferably between about 5 and 25 ml/g.

The reaction may be run for a sufficient time to get the desired conversion. The preferred reaction times are between 1 and 48 hours or more, preferably between about 5 and 24 hours, with between about 15 to 20 hours most preferred.

This process can be done in either a continuous or batch mode.

In this process up to about 50 percent by weight of the N-alkylcarbonyl-5-alkylcarbonylpyrrolidin-2-one is converted to the 5-(1-alkylcarbonyloxy)alkylpyrrolidin-2-one product, the rest of the material recovered is the unreacted starting reagent. The product can be recovered by conventional methods, for example, distillation or recrystallization.

N-alkylcarbonyl-5-alkylcarbonylpyrrolidin-2-one can be prepared in the following manner. A 2-aminoalkane-1,5-dicarboxylic acid which corresponds to the formula

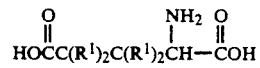

is reacted with an anhydride which corresponds to the formula

in the presence of a tertiary amine catalyst at a temperature of about 60° C. (see Example 1).

In the embodiment wherein $R^1$ is hydrogen and $R^2$ is methyl, glutamic acid is reacted with acetic anhydride to prepare N-acetyl-5-acetylpyrrolidin-2-one.

The 5-(1-alkylcarbonyloxy)alkylpyrrolidin-2-one can be pyrolyzed at a temperature of between about 200° C. and 600° C., preferably between about 450° C. and 550° C., to prepare a 5-(1,2-ethylenically unsaturated)alkylpyrrolidin-2-one. In the embodiment wherein $R^1$ is hydrogen and $R^2$ is methyl, the product is 5-ethenylpyrrolidin-2-one.

The 5-(1,2-ethylenically unsaturated)alkylpyrrolidin-2-one can be contacted with a strong acid at temperatures in excess of 60° C. so as to hydrolyze the pyrrolidin-2-one to prepare a 4-amino-5-alkenoic acid. 4-Amino-5-alkenoic acids are pharmacologically active compounds. In the embodiment wherein $R^1$ is hydrogen and $R^2$ is methyl, the 4-amino-5-alkenoic acid is 4-amino-5-hexenoic acid.

A surprising aspect of this invention is the migration of the alkylcarbonyl moiety from the nitrogen atom of the pyrrolidinone ring to the oxygen of the carbonyl group on the alkylcarbonyl group on the 5 carbon of the pyrrolidin-2-one. This unexpected migration results in the preparation of the 5-(1-alkylcarbonyloxy)alkylpyrrolidin-2-one which can be pyrolyzed to prepare a 5-(1,2-ethylenically unsaturated)alkylpyrrolidin-2-one.

SPECIFIC EMBODIMENTS

The following examples are included for illustrative purposes only and are not intended to limit the scope of the invention or the claims. All parts and percentages are by weight unless otherwise specified.

EXAMPLE 1

A. Preparation of 1,5-Diacetylpyrrolidin-2-one

A mixture of L-glutamic acid (40 g, 0.272 mole), triethylamine (100 ml), acetic anhydride (100 ml) and 4-(dimethylamino)pyridine (0.25 g) is heated at 60° C. with magnetic stirring overnight. The dark solution is removed of volatile materials by distillation at 85° C. at 10 mm Hg. The residue is mixed with 50 ml of 10 percent HCl and extracted with methylene chloride (2×100 ml). The methylene chloride solution is washed with saturated brine and dried over anhydrous magnesium sulfate. After removal of the drying agent and the solvent, the residue is subjected to vacuum distillation to give 30.5 g (66 percent yield) of the desired product, b.p. (0.1 mm) 90° C.-92° C., which solidified rapidly on standing.

B. Preparation of 5-(1-Acetoxyethyl)pyrrolidin-2-one

A mixture of 1,5-diacetylpyrrolidin-2-one (3.5 g), 5 percent platinum on alumina (1.0 g) and acetic acid (30 ml) is stirred in a 200-ml Parr ® pressure vessel under a hydrogen atmosphere (570 psi) at 90° C. for 17.5 hours. Analysis of the reaction mixture after the removal of catalyst and solvent by nuclear magnetic resonance shows that it is a 1:1 mixture of the reactant and the desired product.

EXAMPLE 2

Preparation of 5-(1-Acetoxyethyl)pyrrolidin-2-one 1,5-Diacetylpyrrolidin-2-one (10.6 g) is hydrogenated at 875 psi at 100° C. over 0.5 g of platinum dioxide in 50 ml of ethyl acetate. The conversion after about 17 hours is about 40 percent. The mixture is freed of the catalyst and solvent and is then hydrogenated again in 50 ml of acetic acid over 1.0 g of platinum dioxide for about 19 hours. The conversion is now about 50 percent by nuclear magnetic resonance analysis. This product mixture is distilled at 0.15 mm Hg to give 5.35 g (50 percent), of unreacted 1,5-diacetylpyrrolidin-2-one. The residue upon bulb-to-bulb distillation (140° C. bath temperature, 0.15 mm) gives 4.85 g (46 percent yield, 92 percent selectivity) of 5-(1-acetoxyethyl)pyrrolidin-2-one, containing a very small amount of 1,5-diacetylpyrrolidin-2-one.

What is claimed is:

1. A process for the preparation of a 5-(1-alkylcarbonyloxy)alkylpyrrolidin-2-one which comprises contacting a N-alkylcarbonyl-5-alkylcarbonylpyrrolidin-2-one with hydrogen in the presence of a catalytic amount of a hydrogenation catalyst under conditions such that a 5-(1-alkylcarbonyloxy)alkylpyrrolidin-2-one is prepared.

2. The process of claim 1 wherein the N-alkylcarbonyl-5-alkylcarbonylpyrrolidin-2-one corresponds to the formula

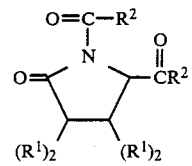

and the 5-(1-alkylcarbonyloxy)alkylpyrrolidin-2-one corresponds to the formula

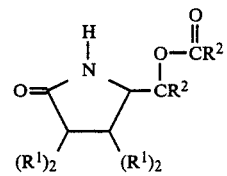

wherein $R^1$ separately in each occurrence is hydrogen or $C_{1-20}$ alkyl and $R^2$ is $C_{1-20}$ alkyl.

3. The process of claim 2 wherein $R^1$ is hydrogen or $C_{1-5}$ alkyl and $R^2$ is $C_{1-5}$ alkyl.

4. The process of claim 2 wherein $R^1$ is hydrogen and $R^2$ is methyl.

5. The process of claim 2 wherein the reaction is run in an organic solvent which is inert to the reactants and not reducible by hydrogen.

6. The process of claim 5 wherein the hydrogenation catalyst is a Group VIII metal, chromium, rhenium or iron.

7. The process of claim 6 wherein the hydrogenation catalyst is palladium or platinum.

8. The process of claim 7 wherein the hydrogenation catalyst is palladium.

9. The process of claim 8 wherein the hydrogenation catalyst is a heterogeneous catalyst.

10. The process of claim 9 wherein the support is a zeolite, silica, alumina or activated carbon.

11. The process of claim 10 wherein the support is alumina.

12. The process of claim 10 wherein the support is loaded with between about 0.1 and 25 percent by weight of the catalyst.

13. The process of claim 12 wherein the support is loaded with between about 0.5 and 10 percent by weight of a hydrogenation catalyst.

14. The process of claim 12 wherein the temperature is between about 25° C. and 200° C.

15. The process of claim 14 wherein the temperature is between about 50° C. and 150° C.

16. The process of claim 14 wherein the pressure is between about 14.7 and 3,000 psi.

17. The process of claim 16 wherein the pressure is between about 50 and 1,500 psi.

18. The process of claim 16 wherein the organic solvent is an alcohol, ether, ester, aromatic hydrocarbon or carboxylic acid.

19. The process of claim 18 wherein the organic solvent is a monocarboxylic acid.

* * * * *